US008517951B2

(12) United States Patent
Fujii et al.

(10) Patent No.: US 8,517,951 B2
(45) Date of Patent: Aug. 27, 2013

(54) BLOOD PRESSURE INFORMATION MEASUREMENT DEVICE AND METHOD OF CALCULATING ARTERIAL STIFFNESS INDEX WITH THE DEVICE

(75) Inventors: Kenji Fujii, Kobe (JP); Tatsuya Kobayashi, Otsu (JP); Toshihiko Ogura, Inuyama (JP)

(73) Assignee: Omron Healthcare Co., Ltd., Kyoto (JP)

( * ) Notice: Subject to any disclaimer, the term of this patent is extended or adjusted under 35 U.S.C. 154(b) by 0 days.

(21) Appl. No.: 13/876,301

(22) PCT Filed: Jul. 4, 2011

(86) PCT No.: PCT/JP2011/065288
§ 371 (c)(1),
(2), (4) Date: Mar. 27, 2013

(87) PCT Pub. No.: WO2012/043002
PCT Pub. Date: Apr. 5, 2012

(65) Prior Publication Data
US 2013/0184596 A1 Jul. 18, 2013

(30) Foreign Application Priority Data
Sep. 28, 2010 (JP) ................. 2010-217306

(51) Int. Cl.
*A61B 5/02* (2006.01)
(52) U.S. Cl.
USPC ........................................................ 600/490
(58) Field of Classification Search
USPC ........................... 600/483, 485, 490
See application file for complete search history.

(56) References Cited

U.S. PATENT DOCUMENTS

| 2003/0004422 A1* | 1/2003 | Narimatsu | 600/500 |
| 2003/0167014 A1* | 9/2003 | Ogura | 600/513 |
| 2006/0229519 A1 | 10/2006 | Fujiwara et al. | |
| 2007/0016083 A1* | 1/2007 | Hasegawa | 600/483 |

(Continued)

FOREIGN PATENT DOCUMENTS

| JP | 2000-316821 A | 11/2000 |
| JP | 2004-113593 A | 4/2004 |

(Continued)

OTHER PUBLICATIONS

Official Communication issued in International Patent Application No. PCT/JP2011/065288, mailed on Oct. 11, 2011.

(Continued)

*Primary Examiner* — Patricia Mallari
*Assistant Examiner* — Etsub Berhanu
(74) *Attorney, Agent, or Firm* — Keating & Bennett, LLP (57) ABSTRACT

A CPU of a blood pressure information measurement device calculates blood pressure from a change in internal pressure of an air bladder used to measure the blood pressure. AI (augmentation index) and Tr (traveling time to reflected wave) are calculated from a pulse wave waveform. A path difference calculation unit of the CPU stores a correction equation to correct a pulse wave propagation distance that is stored in advance, and, by substituting the calculated blood pressure value, AI and the like into the correction equation, corrects the pulse wave propagation distance stored in advance and approximates the pulse wave propagation distance stored in advance to an actual pulse wave propagation distance. A PWV (pulse wave velocity) calculation unit calculates the PWV using the corrected distance.

11 Claims, 9 Drawing Sheets

(56) References Cited

U.S. PATENT DOCUMENTS

| | | |
|---|---|---|
| 2010/0121204 A1 | 5/2010 | Utsuno et al. |
| 2011/0160599 A1* | 6/2011 | Kobayashi et al. ........... 600/494 |
| 2011/0208073 A1 | 8/2011 | Matsukawa et al. |
| 2011/0230774 A1* | 9/2011 | Kobayashi et al. ........... 600/493 |

FOREIGN PATENT DOCUMENTS

| | | |
|---|---|---|
| JP | 2006-288504 A | 10/2006 |
| JP | 2008-246010 A | 10/2008 |
| WO | 2010/024418 A1 | 3/2010 |

OTHER PUBLICATIONS

Mitchell et al., "Changes in Arterial Stiffness and Wave Reflection With Advancing Age in Healthy Men and Women: The Framingham Heart Study", Hypertension, Journal of the American Heart Association, May 3, 2004, pp. 1239-1245.

Segers et al., "Assessment of pressure wave reflection: getting the timing right!", Physiological Measurement, vol. 28, 2007, pp. 1045-1056.

* cited by examiner

BLOOD PRESSURE INFORMATION MEASUREMENT DEVICE AND METHOD OF CALCULATING ARTERIAL STIFFNESS INDEX WITH THE DEVICE

BACKGROUND OF THE INVENTION

1. Field of the Invention

The present invention relates to a blood pressure information measurement device and a method of calculating an arterial stiffness index with the blood pressure information measurement device. More particularly, the present invention relates to a blood pressure information measurement device that measures blood pressure information and effectively determines a degree of arterial stiffness, and a method of calculating an arterial stiffness index with the blood pressure information measurement device.

2. Description of the Related Art

Heretofore, as a device for determining the degree of arterial stiffness, JP 2000-316821A, for example, discloses a device that examines the propagation velocity of a pulse wave ejected from the heart (hereinafter, PWV).

By placing cuffs or the like for measuring the pulse waves at two or more locations such as the upper arm and the lower leg, for example, and measuring the pulse waves simultaneously, PWV is calculated from the difference in times of the pulse waves at the respective locations and the length of the artery between the two points at which the cuffs or the like for measuring the pulse waves are placed. Thus, at least two locations for placing cuffs or the like are needed, and it is difficult to easily measure PWV at home.

In view of this, as a device for determining the degree of arterial stiffness from the pulse wave measured at the location of the upper arm, JP 2004-113593A, for example, discloses a device provided with a cuff for pulse wave measurement and a compression cuff for compressing the distal side. The difference in times of an ejected wave and a reflected wave can be detected using not only the pressure pulse wave measured at the upper arm but also the pulse wave measured by tonometry at the carotid artery or the radial artery.

With the device of JP 2004-113593A, pulse wave velocity serving as an index for determining the degree of arterial stiffness is calculated by separating the ejected wave that is been ejected by the heart from the reflected wave that is reflected by the main reflection site in the aorta by measuring the pulse wave on the side on which the heart is located while compressing the distal side, and detecting the difference in appearance times of the ejected wave and the reflected wave (referred to as Δt, PTT, Tr, etc.). Specifically, the difference in respective propagation paths of the ejected wave and the reflected wave to the measurement site is converted to a pulse wave velocity (PWV), serving as an index for determining the degree of arterial stiffness, by being divided by the time difference between an appearance of the ejected wave and an appearance of the reflected wave at the measurement site.

In such a device, information on the pulse wave propagation distances is needed in addition to the pulse wave propagation times in order to accurately calculate the pulse wave velocity. If the propagation times are the same, this indicates a high degree of arterial stiffness, since propagation velocity increases as propagation distance increases.

Conventionally, the main reflection site of the pulse wave in the aorta is said to be the iliac artery bifurcation. In view of this, a distance (2L_da) obtained by doubling the distance (L_da) from the aortic root to the iliac artery bifurcation was assumed to be the difference in respective propagation paths of the ejected wave and the reflected wave to the measurement site, and a value (2L_da/Tr) obtained by dividing this difference by Tr (Traveling time to reflected wave) was considered to be equal to the PWV of the aorta.

However, the main reflection site is, in fact, not fixed but changes due to differing attributes of the person being measured, such as age and height, and the clinical condition of the person being measured, such as the extent of arterial stiffness. Thus, there is a problem in that an error occurs in the calculated PWV when the reflection site is assumed to be the same for all people.

SUMMARY OF THE INVENTION

In view of problems described above, preferred embodiments of the present invention provide a blood pressure information measurement device that is accurately calculates an index effective in determining the degree of arterial stiffness that is obtained using the pulse wave propagation distance by correcting the pulse wave propagation distance, and a method of calculating an arterial stiffness index with the blood pressure information measurement device.

According to a preferred embodiment of the present invention, a blood pressure information measurement device that calculates, as blood pressure information, a pulse wave velocity that is an arterial stiffness index of a subject includes an air bladder arranged to be placed on a measurement site of the subject, an adjustment device arranged to adjust an internal pressure of the air bladder, and an arithmetic operation device arranged and programmed to calculate the pulse wave velocity of the subject based on a change in the internal pressure of the air bladder. The arithmetic operation device is programmed to execute an arithmetic operation to obtain a blood pressure value of the subject from the change in internal pressure, an arithmetic operation to obtain a pulse wave waveform for one beat from the change in internal pressure, an arithmetic operation to obtain a time difference between an appearance of an ejected wave and an appearance of a reflected wave in the pulse wave waveform for one beat, an arithmetic operation to determine a difference in respective propagation paths of the ejected wave and the reflected wave from a heart to the measurement site based on the blood pressure value and a value representing a distance from an aortic root to an iliac artery bifurcation that is stored in advance, and an arithmetic operation to obtain the pulse wave velocity of the subject based on the propagation path difference and the time difference.

Preferably, the arithmetic operation device, in the arithmetic operation to determine the propagation path difference, determines the propagation path difference using a value representing a characteristic of a shape of the pulse wave waveform, in addition to using the blood pressure value and the value representing the distance from the aortic root to the iliac artery bifurcation.

Preferably, the blood pressure information measurement device further includes an input device to receive a value representing an attribute related to the blood pressure information of the subject, and the arithmetic operation device, in the arithmetic operation to determine the propagation path difference, determines the propagation path difference using the value representing the attribute, in addition to using the blood pressure value and the value representing the distance from the aortic root to the iliac artery bifurcation.

Preferably, the blood pressure information measurement device further includes an input device to receive a value representing an attribute related to the blood pressure information of the subject, and the arithmetic operation device, in the arithmetic operation to determine the propagation path difference, determines the propagation path difference using a value representing a characteristic of a shape of the pulse wave waveform and the value representing the attribute, in addition to using the blood pressure value and the value representing the distance from the aortic root to the iliac artery bifurcation.

Preferably, the arithmetic operation device is arranged and programmed to further execute an arithmetic operation to obtain an AI (augmentation index) value that is a ratio of an amplitude of the ejected wave and an amplitude of the reflected wave from the shape of the pulse wave waveform, and, in the arithmetic operation to determine the propagation path difference, uses the AI value as the value representing a characteristic of the shape of the pulse wave waveform.

Preferably, the value representing the attribute related to the blood pressure information of the subject is at least one of an age of the subject and a height of the subject.

Preferably, the arithmetic operation device, in the arithmetic operation to determine the propagation path difference, calculates the propagation path difference by multiplying the value representing the distance from the aortic root to the iliac artery bifurcation that is stored in advance by a value obtained from the blood pressure value.

Preferably, the air bladder arranged to be placed on the measurement site of the subject includes a first air bladder that is positioned on a proximal side and a second air bladder that is positioned on a distal side when the air bladder is placed on the measurement site. The arithmetic operation device, when performing the arithmetic operation to obtain the pulse wave waveform, obtains the pulse wave waveform from the change in internal pressure of the first air bladder in a state where the distal side of the measurement site is avascularized by the second air bladder.

According to another preferred embodiment of the present invention, a method of calculating an arterial stiffness index in a blood pressure information measurement device that calculates a pulse wave velocity as an arterial stiffness index in a blood pressure information measurement device, the blood pressure information measurement device including an air bladder arranged to be placed on a measurement site of a subject and an arithmetic operation device programmed to calculate the pulse wave velocity of the subject, includes the following steps executed by the arithmetic operation device: calculating a blood pressure value of the subject from a change in internal pressure of the air bladder placed on the measurement site of the subject, obtaining a pulse wave waveform for one beat from the change in internal pressure, specifying a time difference between an appearance of an ejected wave and an appearance of a reflected wave in the pulse wave waveform for one beat, determining a difference in respective propagation paths of the ejected wave and the reflected wave from the heart to the measurement site, based on the blood pressure value and a value representing a distance from an aortic root to an iliac artery bifurcation that is stored in advance, and calculating the pulse wave velocity of the subject based on the propagation path difference and the time difference.

According to various preferred embodiments of the present invention, an index effective in determining the degree of arterial stiffness that is obtained using the pulse wave propagation distance is accurately computed.

The above and other elements, features, steps, characteristics and advantages of the present invention will become more apparent from the following detailed description of the preferred embodiments with reference to the attached drawings.

DETAILED DESCRIPTION OF THE PREFERRED EMBODIMENTS

Hereinafter, preferred embodiments of the present invention will be described with reference to the drawings. In the following description, the same reference signs are given to components and constituent elements that are the same. The names and functions thereof are also the same.

Pulse wave velocity (hereinafter, PWV) is an exemplary index used to determine the degree of arterial stiffness. The difference in respective propagation paths of an ejected wave and a reflected wave to a measurement site is converted to PWV by being divided by the time difference between the appearance of the ejected wave and the appearance of the reflected wave at the measurement site.

With a conventional PWV calculation method, a distance (2L_da) obtained by doubling the distance (L_da) from the aortic root to the iliac artery bifurcation was assumed to be the difference in respective propagation paths of the ejected wave and the reflected wave to the measurement site, and PWV was given by a value (2L_da/Tr) obtained by dividing this difference by Tr.

However, the main reflection site is, in fact, not fixed but changes due to differences in the actual length of the vascular channel of a person resulting from age, height and the like, and to the degree of arterial stiffness of a person resulting from age, clinical condition and the like. For example, in a paper entitled "Changes in arterial stiffness and wave reflection with advancing age in healthy men and women: the Framingham Heart Study," (Hypertension. 2004; 43: 1239-1245) by Mitchell et al., it is shown that the reflection site moves further from the heart with advancing age. On the other hand, in a paper entitled "Assessment of pressure wave reflection: getting the timing right!" (Physiol. Meas. 28 (2007) 1045-1056) by Segers et al., results are also shown indicating that the reflection site moves closer to the heart with advancing age. An error will thus occur in the calculated PWV when the same reflection site is assumed for all people.

Figure 1:
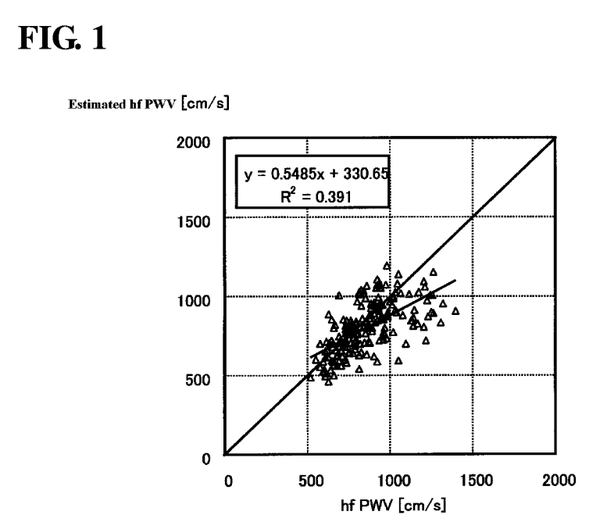
FIG. 1 is a diagram showing a relationship between measured PWV values and estimated PWV values for the same person.

FIG. 1 is a diagram showing the relationship between measured PWV values and estimated values for the same person. Here, heart-femoral PWV (hfPWV) calculated from the pulse wave measured at the two points of the heart and the femoral artery is used as PWV. The "measured values" are PWV values calculated from the pulse wave measured at the two points of the heart and the femoral artery. The "estimated values" are values calculated using a pulse wave propagation time calculated from the pulse wave measured by tonometry at the one point of the carotid artery and the distance (L_da) from the aortic root to the iliac artery bifurcation. In FIG. 1, the horizontal axis represents measured values and the vertical axis represents estimated values.

It is clear from FIG. 1 that there are people whose measured value and estimated value differ greatly. This is conceivably due to an error being included in the estimated value. One conceivable cause of the error in the estimated value is an error in the assumed reflected wave path difference.

The inventors of the present invention calculated, for every person being measured, a "relative distance", a systolic blood pressure, and an AI (augmentation index) value, which is a ratio of the amplitude of the reflected wave to the amplitude of the ejected wave using, as the "relative distance", a ratio (L_Tr/L_da) of the distance (L_Tr) from the aortic root to the actual reflection position calculated from measured hfPWV and Tr relative to the distance (L_da) from the aortic root to the iliac artery bifurcation in the case where the iliac artery bifurcation is assumed to be the reflection site. Relative distance=1 indicates that the assumed reflection position and the actual reflection position are equal.

Note that the distance (L_Tr) is calculated by the following equation (1):

$$L\_Tr = hfPWV \times Tr/2 \quad (1)$$

Figure 2A:
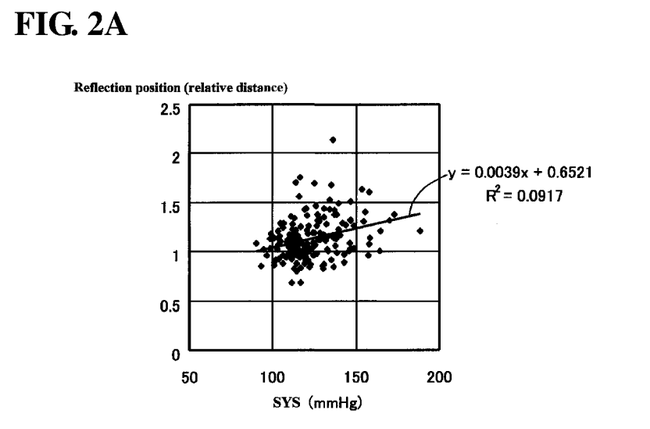
FIG. 2A is a diagram showing a relationship between "relative distances" and systolic blood pressures for a plurality of people.
Figure 2B:
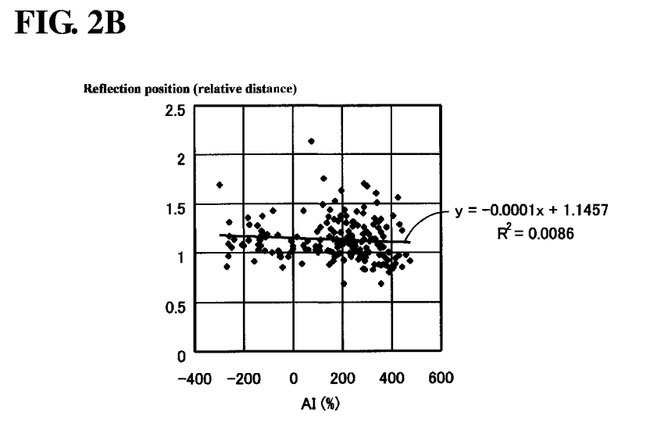
FIG. 2B is a diagram showing a relationship between "relative distances" and AI values for a plurality of people.

FIG. 2A is a diagram showing a relationship between "relative distances" and systolic blood pressures for a plurality of people, and FIG. 2B shows a relationship between "relative distances" and AI values for a plurality of people. It is clear from FIG. 2A and FIG. 2B that the calculated relative distance differs for every person, and that relative distance=1 is, in fact, not necessarily achieved. Furthermore, from the relationships shown in FIG. 2A and FIG. 2B, the inventors discovered, in particular, that relative distance increases as blood pressure increases, and that relative distance decreases as AI value increases. That is, the inventors discovered that the actual reflection position deviates from the assumed reflection position due also to blood pressure values and characteristics of the shape of the blood pressure waveform, in addition to attributes related to the vascular channel of the person such as height and age.

Figure 3:
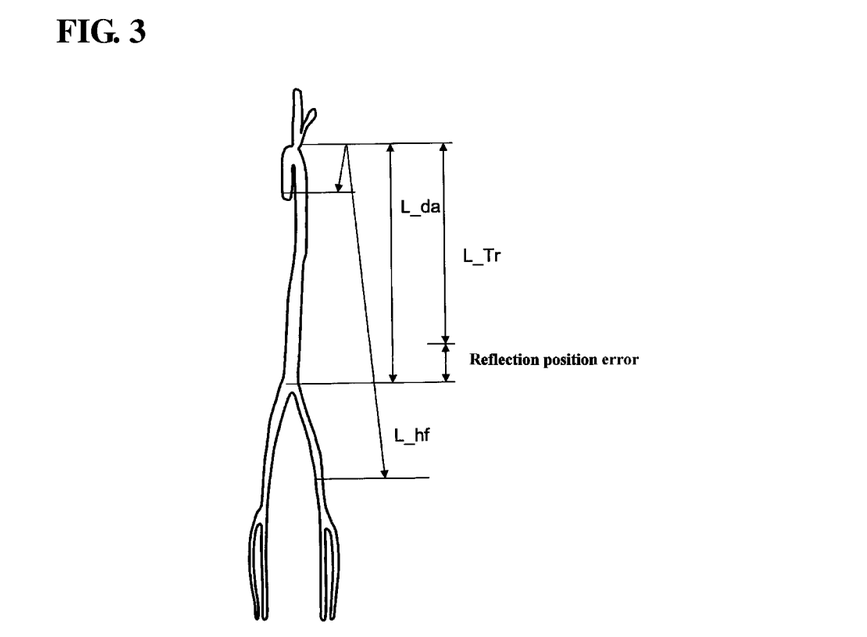
FIG. 3 is a schematic diagram representing a distance (L_da) from the aortic root to the iliac artery bifurcation, a distance (L_Tr) from the aortic root to the actual reflection position calculated from measured hfPWV and Tr, and a distance (L_hf) of a vascular channel between the two points of the heart and the femoral artery serving as pulse wave measurement sites.

FIG. 3 is a schematic diagram representing the distance (L_da) from the aortic root to the iliac artery bifurcation, the distance (L_Tr) from the aortic root to the actual reflection position calculated from measured hfPWV and Tr, and the distance (L_hf) of the vascular channel between the two points of the heart and the femoral artery serving as pulse wave measurement sites.

As is clear from FIG. 3, an increase in "relative distance", being synonymous with the distance (L_Tr) becoming longer than the distance (L_da), means that the actual reflection position is further from the heart than the assumed reflection position. In contrast, a decrease in "relative distance", being synonymous with the distance (L_Tr) becoming shorter than the distance (L_da), means that the actual reflection position is closer to the heart than the assumed reflection position.

The inventors decided to obtain the distance (L_Tr) from the aortic root to the actual reflection position by correcting the distance (L_da) from the aortic root to the iliac artery bifurcation using attributes related to the vascular channel of the person such as height and age, a blood pressure value, and a characteristic of the shape of the blood pressure waveform, and to determine the reflected wave path difference therefrom.

As a first example, the distance (L_Tr) from the aortic root to the actual reflection position is obtained by correcting the distance (L_da) using a blood pressure value of the person being measured, and a characteristic of the shape of the blood pressure waveform. As a specific example, the distance (L_Tr) is calculated by the following equation (2), using systolic blood pressure as the blood pressure value of the person, and using the AI value as a value representing a characteristic of the shape of the blood pressure waveform:

$$L\_Tr = (A \times SYS + B \times AI + C) \times L\_da \quad (2)$$

Also, as a second example, the distance (L_da) is corrected using a blood pressure value of the person being measured. As a specific example, the distance (L_Tr) is calculated by the following equation (3), using systolic blood pressure as the blood pressure value of the person:

$$L\_Tr = (A' \times SYS + C') \times L\_da \quad (3)$$

Note that coefficients empirically obtained from the results of measuring an actual group of people can be used for coefficients A, A', B, C, and C'. Also, a measured value of the distance from the aortic root to the iliac artery bifurcation or a value derived by approximation of the measured value and a height of the person derived in advance can be used for the distance (L_da) from the aortic root to the iliac artery bifurcation.

Also, as a third example, the distance (L_da) is corrected using attributes related to the vascular channel of the person being measured, a blood pressure value of the person being measured, and a characteristic of the shape of the blood pressure waveform. As a specific example, the distance (L_Tr) is calculated by the following equation (4), using age and height as attributes related to the vascular channel of the person, using systolic blood pressure as the blood pressure value of the person, and using the AI value as a value representing a characteristic of the shape of the blood pressure waveform:

$$L\_Tr=(D\times \text{age}+E\times SYS+F\times AI+G\times \text{height}+H)\times L\_da \quad (4)$$

Also, as a fourth example, the distance (L_da) is corrected using attributes related to the vascular channel of the person being measured, and using a blood pressure value of the person being measured. As a specific example, the distance (L_Tr) is calculated by the following equation (5), using age and height as attributes related to the vascular channel of the person, and using systolic blood pressure as the blood pressure value of the person:

$$L\_Tr=(D'\times \text{age}+E'\times SYS+G'\times \text{height}+H')\times L\_da \quad (5)$$

Note that coefficients empirically obtained from the results of measuring an actual group of people can also be used for the coefficients D, D', E, E', F, G, G', H, and H'.

Note that although systolic blood pressure is preferably used as the blood pressure value of the person being measured in the above description, diastolic blood pressure may be used, or an intermediate value between systolic blood pressure and diastolic blood pressure may be used, for example. Also, although the AI value is preferably used as the value representing a characteristic of the shape of the blood pressure waveform of the person being measured, another index such as Tr or the like may be used, for example. Also, although age and height are preferably used as attributes related to the vascular channel of the person being measured, one of height and age may be used, or other attributes may be used, for example.

Figure 4:
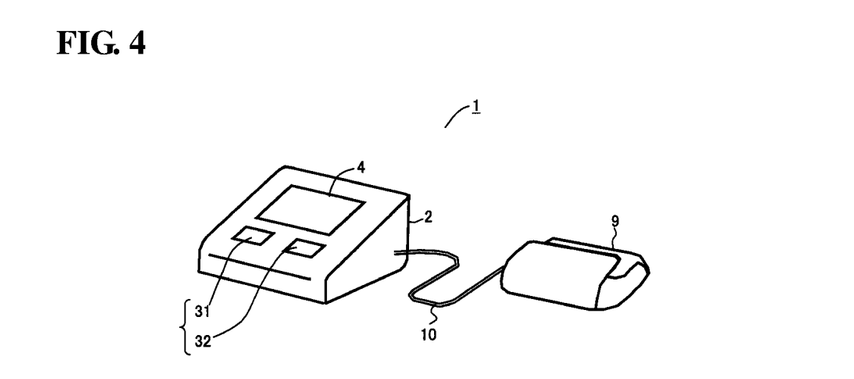
FIG. 4 is a diagram showing a specific example of the external appearance of a blood pressure information measurement device (hereinafter abbreviated as "measurement device") according to a preferred embodiment of the present invention.

FIG. 4 is a diagram showing a specific example of the external appearance of a blood pressure information measurement device (hereinafter, measurement device) 1 according to a preferred embodiment of the present invention.

Referring to FIG. 4, the measurement device 1 includes a base 2 connected to an air tube 10, and an arm band 9 that is placed on the upper arm, which is the measurement site. An operation unit 3 that is operated in order to provide various instructions to a display unit 4 to display various information including measurement results and to the measurement device 1 is arranged on the front of the base 2. The operation unit 3 includes a switch 31 that is operated in order to switch power on/off, and a switch 32 that is operated in order to instruct the start of measurement.

Figure 5A:
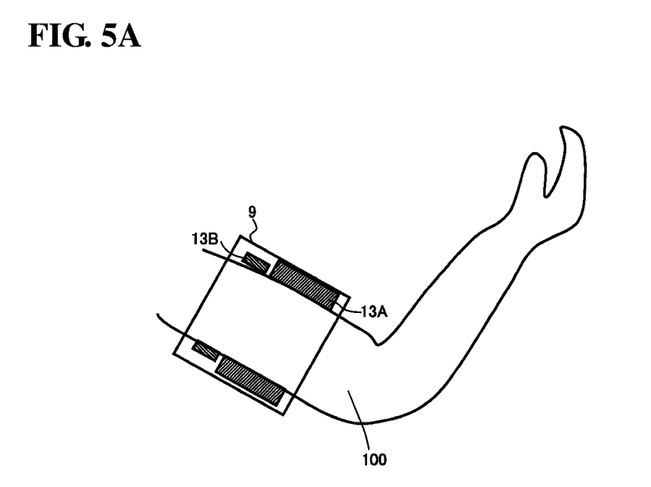
FIG. 5A is a diagram showing a specific example of a measurement posture.
Figure 5B:
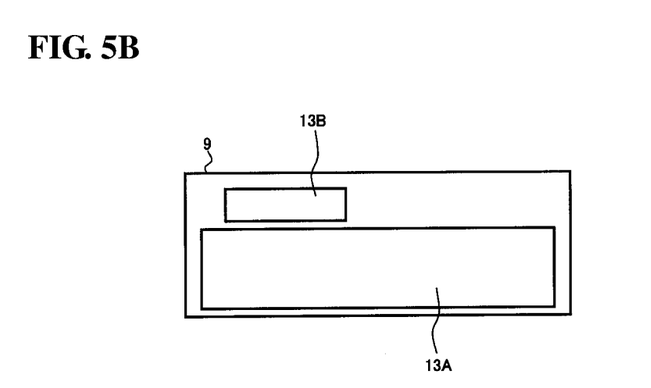
FIG. 5B is a diagram showing a specific example of the configuration of an arm band.

Referring to FIG. 5A and FIG. 5B, the arm band 9 is provided with air bladders serving as fluid bladders to compress the body of the person being measured. The air bladder includes an air bladder 13A, which is a fluid bladder that is used in order to measure blood pressure as blood pressure information, and an air bladder 13B, which is a fluid bladder that is used in order to measure pulse wave as blood pressure information. The size of the air bladder 13B preferably is, as an example, about 20 mm×about 200 mm. Also, the air volume of the air bladder 13B preferably is less than or equal to about one fifth of the air volume of the air bladder 13A, for example.

When measuring the pulse wave using the measurement device 1, the arm band 9 is wrapped around an upper arm 100 serving as the measurement site, as shown in FIG. 5A. Through the switch 32 being pressed in this state, blood pressure information is measured, and an index to determine the degree of arterial stiffness is calculated based on the blood pressure information. Here, "blood pressure information" denotes information related to blood pressure that is obtained through measurements taken from the body, and, specifically, corresponds to blood pressure value, blood pressure waveform (pulse wave waveform), heart rate, and the like.

Figure 6:
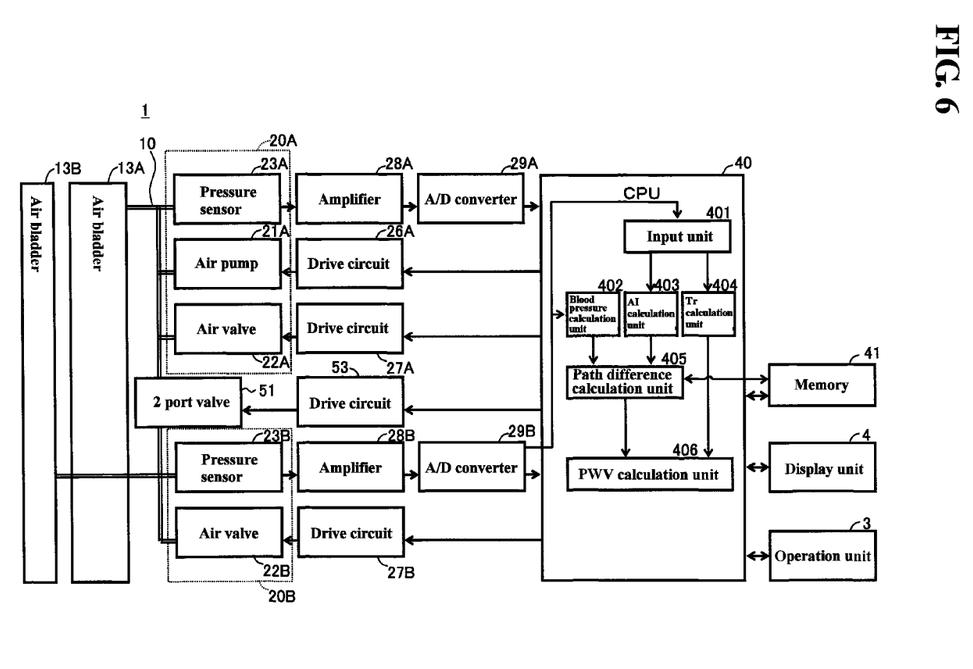
FIG. 6 is a block diagram showing an exemplary configuration of the measurement device.

FIG. 6 is a block diagram showing an exemplary configuration of the measurement device 1.

Referring to FIG. 6, the measurement device 1 includes an air system 20A that is connected to the air bladder 13A via the air tube 10, an air system 20B that is connected to the air bladder 13B via the air tube 10, and a CPU (Central Processing Unit) 40. The air system 20A includes an air pump 21A, an air valve 22A, and a pressure sensor 23A. The air system 20B includes an air valve 22B and a pressure sensor 23B.

The air pump 21A is connected to a drive circuit 26A, and the drive circuit 26A is further connected to the CPU 40. The air pump 21A is driven by the drive circuit 26A upon receiving a command from the CPU 40, and inflates the air bladder 13A by sending compressed gas into the air bladder 13A.

The air valve 22A is connected to a drive circuit 27A, and the drive circuit 27A is further connected to the CPU 40. The air valve 22B is connected to a drive circuit 27B, and the drive circuit 27B is further connected to the CPU 40. Open and closed states of the air valves 22A and 22B are controlled by the drive circuits 27A and 27B upon receiving a command from the CPU 40. Through the open and closed states being controlled, the air valves 22A and 22B maintain or lower the pressure inside the air bladders 13A and 13B. Thus, the pressure inside the air bladders 13A and 13B is controlled.

The pressure sensor 23A is connected to an amplifier 28A, the amplifier 28A is further connected to an A/D converter 29A, and the A/D converter 29A is further connected to the CPU 40. The pressure sensor 23B is connected to an amplifier 28B, the amplifier 28B is further connected to an A/D converter 29B, and the A/D converter 29B is further connected to the CPU 40. The pressure sensors 23A and 23B respectively detect the pressure inside the air bladders 13A and 13B, and output signals that depend on the detected values to the amplifiers 28A and 28B. The output signals are input to the CPU 40 after being amplified by the amplifiers 28A and 28B, and digitized by the A/D converters 29A and 29B.

The air tube from the air bladder 13A and the air tube from the air bladder 13B are connected by a 2 port valve 51. The 2 port valve 51 is connected to a drive circuit 53, and the drive circuit 53 is further connected to the CPU 40. The 2 port valve 51 includes a valve for the air bladder 13A and a valve for the air bladder 13B, and these valves open and close through the 2 port valve 51 being driven by the drive circuit 53 upon receiving a command from the CPU 40.

A program that is executed by the CPU 40 is stored in a memory 41. The CPU 40 reads out the program from the memory 41 based on a command input to the operation unit 3 provided in the base 2 of the measurement device, executes the program that was read out, and outputs a control signal in accordance with execution of the program. Also, the CPU 40 outputs measurement results to the display unit 4 or the memory 41. Apart from the measurement results also being stored in the memory 41, attributes related to the vascular channel of the person such as height and age are also stored if needed. The attributes related to the vascular channel of the person being measured are input in advance through operation of the operation unit 3. The CPU 40 then reads out attributes related to the vascular channel of the person being measured in accordance with execution of the program for use in arithmetic operations if needed.

Referring further to FIG. 6, the CPU 40 includes, as functions to calculate PWV as an index to determine the degree of arterial stiffness in accordance with the abovementioned principles, an input unit 401 to receive a pressure signal from the pressure sensor 23B and obtain a blood pressure waveform for one beat, a blood pressure calculation unit 402 to receive a pressure signal from the pressure sensor 23B and calculate a blood pressure value (e.g., systolic blood pressure value), an AI calculation unit 403 to calculate an AI value from the blood pressure waveform, a Tr calculation unit 404 to calculate Tr from the blood pressure waveform, a path difference calculation unit 405 to obtain the distance (L_Tr) by correcting the distance (L_da) from the aortic root to the iliac artery bifurcation using the systolic blood pressure or the systolic blood pressure and the AI value in accordance with equation (2) or equation (3), and determining a reflected wave path difference, and a PWV calculation unit 406 to calculate PWV by dividing the reflected wave path difference by Tr. Although these are functions that preferably are mainly provided by the CPU 40 through the CPU 40 being reading out and executing the program stored in the memory 41 in accordance with an operation signal from the operation unit 3, at least some of these functions may be provided and performed by a hardware configuration, for example.

Figure 7:
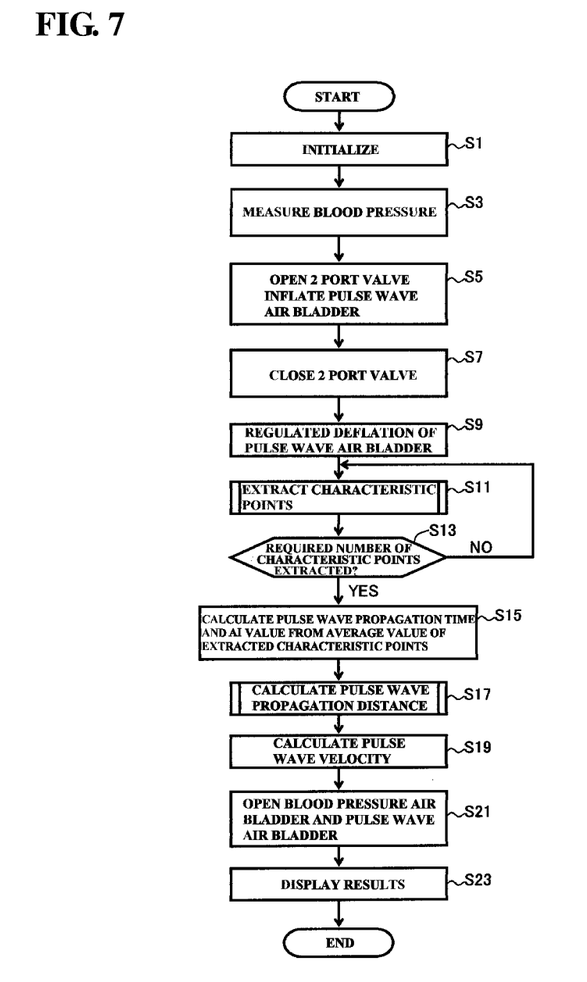
FIG. 7 is a flowchart representing an operation performed by the measurement device.
Figure 9:
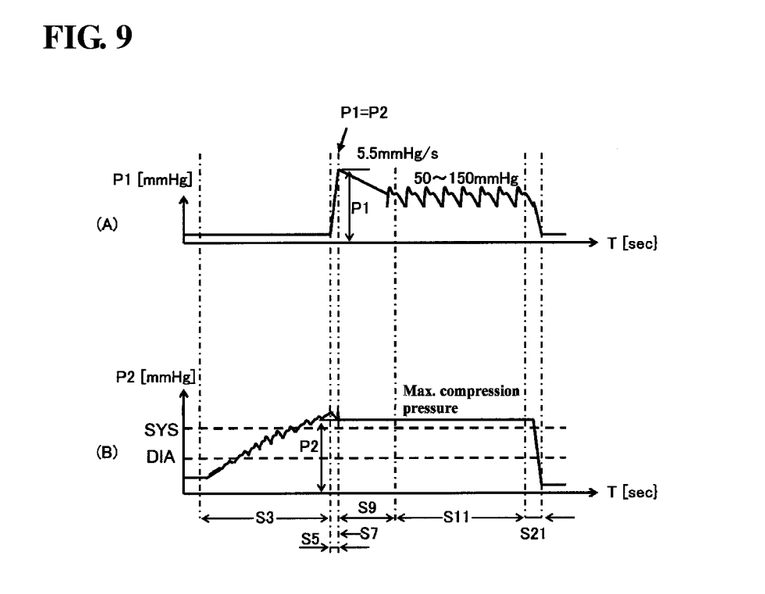
FIG. 9 is a diagram illustrating the change in pressure inside an air bladder for compression and an air bladder for measurement during the operation performed by the measurement device.

FIG. 7 is a flowchart showing an operation performed by the measurement device 1. The operation shown in FIG. 7 is started by the person being measured pressing the switch 32. This operation is performed by the CPU 40 reading out the program stored in the memory 41 and controlling the units that are shown in FIG. 6. Also, the change in pressure inside the air bladders 13A and 13B while the operation is performed by the measurement device 1 will be described using FIG. 9. (A) in FIG. 9 shows the temporal change in a pressure P1 inside the air bladder 13B, and (B) in FIG. 9 shows the temporal change in a pressure P2 inside the air bladder 13A. S3 to S17 along the time axis in (A) and (B) in FIG. 9 coincide with respective operations of the measurement operation performed by the measurement device 1 which will be discussed below.

Referring to FIG. 7, when the operation starts, at step S1 the units are initialized in the CPU 40. At step S3 the CPU 40 outputs a control signal to the air system 20A, starts inflation of the air bladder 13A, and measures blood pressure in the inflation process. As for the measurement of blood pressure at step S3, measurement is performed using an oscillometric method that is performed with a normal sphygmomanometer. At step S3 the CPU 40 calculates the blood pressure value based on the pressure signal from the pressure sensor 23B, and stores the calculated blood pressure value in a predetermined area of the memory 41.

When the measurement of blood pressure at step S3 is completed, at step S5 the CPU 40 outputs a control signal to the drive circuit 53, and causes both the valve for the air bladder 13A and the valve for the air bladder 13B of the 2 port valve 51 to be opened. The air bladder 13A and the air bladder 13B thereby communicate, and some of the air inside the air bladder 13A moves to the air bladder 13B, and the air bladder 13B is inflated.

In the example in (B) of FIG. 9, the pressure P2 inside the air bladder 13A is increased, from the start of inflation at the step S3 until the measurement of blood pressure is completed, until the pressure is higher than the systolic blood pressure value. Thereafter, through the valves of the 2 port valve 51 being opened at step S5, some of the air inside the air bladder 13A moves to the air bladder 13B, and the pressure P2 decreases. Simultaneously, the pressure P1 inside the air bladder 13B increases rapidly, as shown in (A) of FIG. 9. At the point in time when the pressure P1 and the pressure P2 coincide, that is, at the point in time when the internal pressures of the air bladders 13A and 13B are in equilibrium, air stops moving from the air bladder 13A to the air bladder 13B. At step S7 the CPU 40 outputs a control signal to the drive circuit 53 at this time, and causes both of the valves of the 2 port valve 51 that were opened at the step S5 to be closed. In (A) and (B) of FIG. 9, the pressure P1 and the pressure P2 are shown to coincide at the point in time of step S7. Since the volume of the air bladder 13B is small compared with the volume of the air bladder 13A as represented in FIG. 5A, there is not a substantial reduction of the pressure P2 at step S5, and the pressure P1 and the pressure P2 are both higher than the systolic blood pressure at the point in time of step S7.

Thereafter, the CPU 40 outputs a control signal to the drive circuit 27B at step S9, and decreases the pressure P1 inside the air bladder 13B in a regulated manner until a pressure suitable for pulse wave measurement is achieved. Here, the regulated deflation preferably is performed at about 5.5 mmHg(s)/sec, for example. Also, the pressure suitable for pulse wave measurement preferably is about 50 mmHG to about 150 mmHg, for example. Since both the valves of the 2 port valve 51 are closed at this time, the pressure P2 inside the air bladder 13A compresses the distal side of the measurement site at a higher pressure than the systolic blood pressure, as shown in (B) in FIG. 9, achieving an avascularized state.

With the distal side in the avascularized state, at step S11 the CPU 40 performs an operation to extract, every time a blood pressure waveform for one beat based on the pressure signal from the pressure sensor 23B is input, a characteristic point from the blood pressure waveform. That is, at step S11 the CPU 40 receives a pressure signal from the pressure sensor 23B, and specifies a blood pressure waveform for one beat. Note that, the blood pressure waveform for one beat may be specified based on the input of blood pressure waveforms for a plurality of beats, from the average value thereof, or the blood pressure waveform for one beat may be specified from an average value for the pulses represented in the pressure signal input for a predetermined period (several seconds, etc.).

A prescribed point such as a point corresponding to a maxima of a second-order differential curve of the blood pressure waveform, or a point corresponding to the falling zero-crossing point of a fourth-order differential curve of the blood pressure waveform is then extracted as a characteristic point from the specified blood pressure waveform for one beat.

The characteristic point extraction operation of step S11 is repeated every time a blood pressure waveform for one beat is input, until a prescribed number of characteristic points (e.g., for ten beats) required in order to calculate an arterial stiffness index of characteristic points is extracted. During this time, the pressure P1 inside the air bladder 13B is maintained at the pressure suitable for pulse wave measurement as shown in (A) of FIG. 9, and the pressure P2 inside the air bladder 13A is maintained at a higher pressure than the systolic blood pressure as shown in (B) of FIG. 9. The avascularized state of the distal side of the measurement site is thereby maintained.

When the number of the extracted characteristic points reaches the prescribed number (e.g., ten beats) (YES at step S13), at step S15 the CPU 40 calculates the pulse wave propagation time and the AI value using the average value of the extracted characteristic points. That is, Tr is calculated by calculating the time difference from the rising edge of the ejected wave, using, as the rising edge of the reflected wave, a point such as a point corresponding to the maxima of a second-order differential curve of the blood pressure waveform or a point corresponding to the falling zero-crossing point of a fourth-order differential curve of the blood pressure waveform, and the AI value is calculated by specifying the peak magnitude of the ejected wave and the peak magnitude of the reflected wave of the blood pressure waveform for one beat, and calculating the ratio thereof. Note that the time difference (Tpp) between the time of the peak of the ejected wave and the time of the peak of the reflected wave may be used instead of Tr.

Figure 8:
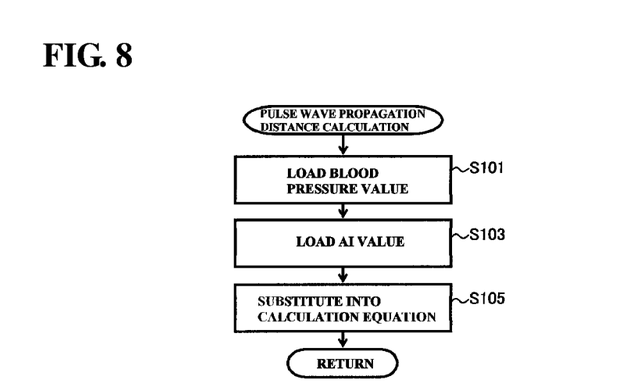
FIG. 8 is a flowchart representing processing performed at step S17 in FIG. 7.

Furthermore, at step S17 the CPU 40 calculates the pulse wave propagation distance. FIG. 8 is a flowchart representing the processing of step S17.

In the case of correcting the distance (L_da) using a blood pressure value of the person being measured and a characteristic of the shape of the blood pressure waveform, shown above as the first example, that is, in the case of calculating the distance (L_Tr) using equation (2), the CPU 40 calculates the distance (L_Tr) from the aortic root to the actual reflection position by reading out the systolic blood pressure value calculated at step S3 (step S101), reading out the AI value calculated at step S15 (step S103), and substituting these values into equation (2) (step S105).

In the case of correcting the distance (L_da) using a blood pressure value of the person being measured, shown above as the second example (i.e., in the case of calculating the distance (L_Tr) using the equation (3)), the operation of step S103 is skipped, and the distance (L_Tr) from the aortic root to the actual reflection position is calculated, by reading out the systolic blood pressure calculated at step S3 (step S101), and by substituting this value into equation (3) (step S105).

In the case of correcting the distance (L_da) using attributes related to the vascular channel of the person being measured, a blood pressure value of the person being measured, and a characteristic of the shape of the blood pressure waveform, shown above as the third example, that is, in the case of calculating the distance (L_Tr) using equation (4), the CPU 40 calculates the distance (L_Tr) from the aortic root to the actual reflection position by further reading out attributes related to the vascular channel of the person being measured such as age and height from the memory 41, in addition to the operations of step S101 and S103, and substituting these values into equation (4) (step S105).

In the case of correcting the distance (L_da) using attributes related to the vascular channel of the person being measured, and a blood pressure value of the person being measured, shown above as the fourth example (i.e., in the case of calculating the distance (L_Tr) using equation (5)), the operation of step S103 is skipped. The CPU 40 calculates the distance (L_Tr) from the aortic root to the actual reflection position by further reading out attributes related to the vascular channel of the person being measured such as age and height from the memory 41, in addition to the operation of step S101, and substituting these values into equation (5) (step S105).

The CPU 40 calculates the difference (2L_Tr) in the respective propagation paths of the ejected wave and the reflected wave from the heart to the measurement site by doubling the calculated distance (L_Tr) from the aortic root to the actual reflection position.

At step S19 the CPU 40 calculates PWV as an arterial stiffness index by dividing the propagation path difference calculated at step S17 by Tr calculated at step S15. At step S21 the CPU 40 then outputs a control signal to the drive circuits 27A and 27B, and causes the air valves 22A and 22B to be opened, thus returning the pressure of the air bladders 13A and 13B to atmospheric pressure. In the example of (A) and (B) in FIG. 9, the pressures P1 and P2 rapidly decrease to atmospheric pressure during the interval of step S21.

Processing to perform display on the display unit 4 provided in the base 2 is performed and the calculated systolic blood pressure value (SYS), diastolic blood pressure value (DIA), arterial stiffness index, and measurement results such as the measured pulse wave are displayed.

In the measurement device 1, the difference in respective propagation paths of the ejected wave and the reflected wave from the heart to the measurement site that is used when calculating pulse wave velocity (PWV) as the degree of stiffening of the arteries of the person being measured is calculated from the distance (L_Tr) from the aortic root to the actual reflection position that is obtained by correcting the distance (L_da) from the aortic root to the iliac artery bifurcation using attributes related to the vascular channel of the person being measured such as height and age, a blood pressure value, a characteristic of the shape of the blood pressure waveform, or a combination thereof.

Figure 10:
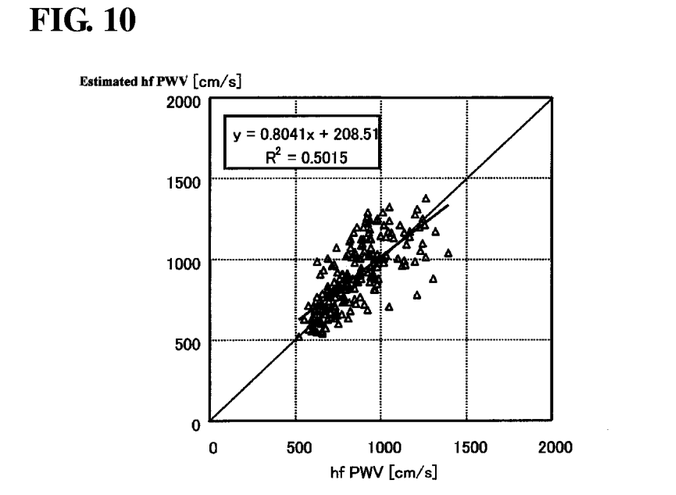
FIG. 10 shows a relationship between estimated PWV values calculated using the distance (L_Tr) obtained by correcting the distance (L_da) using a blood pressure value of the person being measured and measured PWV values.
Figure 11:
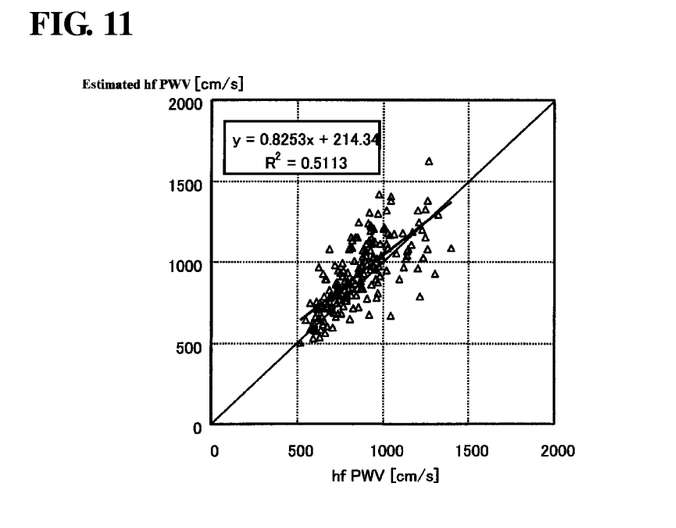
FIG. 11 shows a relationship between estimated PWV values calculated using the distance (L_Tr) obtained by correcting the distance (L_da) using a blood pressure value of the person being measured and an AI value serving as a value representing a characteristic of the shape of the blood pressure waveform and measured PWV values.
Figure 12:
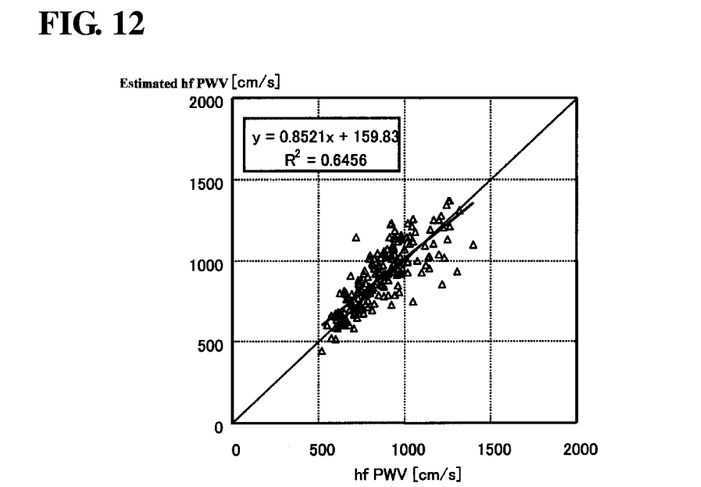
FIG. 12 shows a relationship between estimated PWV values calculated using the distance (L_Tr) obtained by correcting the distance (L_da) using a blood pressure value of the person being measured, an AI value serving as a value representing a characteristic of the shape of the blood pressure waveform, and age and height serving as attributes related to the vascular channel of the person being measured and measured PWV values.

FIGS. 10 to 12 are diagrams showing a relationship between measured PWV values for the same person and estimated PWV values calculated from the pulse wave propagation time and the distance (L_Tr) obtained by correcting the distance (L_da) from the aortic root to the iliac artery bifurcation in the measurement device 1. FIG. 10 shows the relationship between estimated PWV values calculated using the distance (L_Tr) obtained by correcting the distance (L_da) using a blood pressure value of the person being measured, shown above as the second example, and measured PWV values. FIG. 11 shows the relationship between estimated PWV values calculated using the distance (L_Tr) obtained by correcting the distance (L_da) using a blood pressure value of the person being measured and the AI value as a value representing a characteristic of the shape of the blood pressure waveform, shown above as the first example, and measured PWV values. FIG. 12 shows the relationship between estimated PWV values calculated using the distance (L_Tr) obtained by correcting the distance (L_da) using a blood pressure value of the person being measured, the AI value as a value representing a characteristic of the shape of the blood pressure waveform, and age and height as attributes related to the vascular channel of the person being measured, shown above as the third example, and measured PWV values.

Referring to FIGS. 10 to 12, it is clear that in the case where correction is performed using any of the methods in the preferred embodiments of the present invention, the difference between the measured values and the estimated values is markedly smaller, as compared with the relationship between the measured values and the estimated values of PWV, shown in FIG. 1. That is, it is clear that correction according to any of the abovementioned methods approximates the assumed reflection position to the actual reflection position. The error in the calculated PWV can be reduced more than with a conventional method of calculating PWV, and the degree of arterial stiffness can be accurately determined.

Note that, in the above examples, two air bladders, namely, the air bladder 13A, which is a fluid bladder used in order to measure blood pressure, and the air bladder 13B, which is a fluid bladder used in order to measure pulse wave, are preferably provided in the arm band 9, as represented in FIG. 5A and FIG. 5B. However, these air bladders may be replaced with one air bladder, for example. In this case, the CPU 40 measures pulse wave and blood pressure based on the change in internal pressure of the one air bladder.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

The invention claimed is:

1. A blood pressure information measurement device for calculating a pulse wave velocity that is an arterial stiffness index of a subject as blood pressure information, the blood pressure information measurement device comprising:
   an air bladder arranged to be placed on a measurement site of the subject;
   an adjustment device arranged to adjust an internal pressure of the air bladder; and
   an arithmetic operation device arranged and programmed to perform processing to calculate the pulse wave velocity of the subject based on a change in internal pressure of the air bladder; wherein
   the arithmetic operation device is programmed to execute:
   an arithmetic operation to obtain a blood pressure value of the subject from the change in internal pressure;
   an arithmetic operation to obtain a pulse wave waveform for one beat from the change in internal pressure;
   an arithmetic operation to obtain a time difference between an appearance of an ejected wave and an appearance of a reflected wave in the pulse wave waveform for one beat;
   an arithmetic operation to determine a difference in respective propagation paths of the ejected wave and the reflected wave from a heart to the measurement site, based on the blood pressure value and a value representing a distance from an aortic root to an iliac artery bifurcation that is stored in advance; and
   an arithmetic operation to obtain the pulse wave velocity of the subject based on the propagation path difference and the time difference.

2. The blood pressure information measurement device according to claim 1, wherein the arithmetic operation device, in the arithmetic operation to determine the propagation path difference, is programmed to determine the propagation path difference using a value representing a characteristic of a shape of the pulse wave waveform, in addition to using the blood pressure value and the value representing the distance from the aortic root to the iliac artery bifurcation.

3. The blood pressure information measurement device according to claim 2, wherein
   the arithmetic operation device is programmed to execute an arithmetic operation to obtain an augmentation index (AI) value that is a ratio of an amplitude of the ejected wave and an amplitude of the reflected wave from the shape of the pulse wave waveform; and
   in the arithmetic operation to determine the propagation path difference, the arithmetic operation device is programmed to use the AI value as the value representing a characteristic of the shape of the pulse wave waveform.

4. The blood pressure information measurement device according to claim 1, further comprising:
   an input device arranged to receive a value representing an attribute related to the blood pressure information of the subject; wherein
   the arithmetic operation device, in the arithmetic operation to determine the propagation path difference, is programmed to determine the propagation path difference using the value representing the attribute, in addition to using the blood pressure value and the value representing the distance from the aortic root to the iliac artery bifurcation.

5. The blood pressure information measurement device according to claim 4, wherein the value representing the attribute related to the blood pressure information of the subject is at least one of an age of the subject and a height of the subject.

6. The blood pressure information measurement device according to claim 1, further comprising:
   an input device arranged to receive a value representing an attribute related to the blood pressure information of the subject; wherein
   the arithmetic operation device, in the arithmetic operation to determine the propagation path difference, is programmed to determine the propagation path difference using a value representing a characteristic of a shape of the pulse wave waveform and the value representing the attribute, in addition to using the blood pressure value and the value representing the distance from the aortic root to the iliac artery bifurcation.

7. The blood pressure information measurement device according to claim 6, wherein
   the arithmetic operation device is programmed to execute an arithmetic operation to acquire an augmentation index (AI) value that is a ratio of an amplitude of the ejected wave and an amplitude of the reflected wave from the shape of the pulse wave waveform; and
   in the arithmetic operation to determine the propagation path difference, the arithmetic operation device is programmed to use the AI value as the value representing a characteristic of the shape of the pulse wave waveform.

8. The blood pressure information measurement device according to claim 6, wherein the value representing the attribute related to the blood pressure information of the subject is at least one of an age of the subject and a height of the subject.

9. The blood pressure information measurement device according to claim 1, wherein the arithmetic operation device, in the arithmetic operation to determine the propagation path difference, is programmed to calculate the propagation path difference by multiplying the value representing the distance from the aortic root to the iliac artery bifurcation that is stored in advance by a value obtained from the blood pressure value.

10. The blood pressure information measurement device according to claim 1, wherein
    the air bladder arranged to be placed on the measurement site of the subject includes a first air bladder that is positioned on a proximal side and a second air bladder that is positioned on a distal side; and
    the arithmetic operation device, in the arithmetic operation to obtain the pulse wave waveform, is programmed to obtain the pulse wave waveform from the change in internal pressure of the first air bladder in a state in which the distal side of the measurement site is avascularized by the second air bladder.

11. An arterial stiffness index calculation method for calculating a pulse wave velocity as an arterial stiffness index in a blood pressure information measurement device, the blood pressure information measurement device including an air bladder arranged to be placed on a measurement site of a subject and an arithmetic operation device to perform processing to calculate the pulse wave velocity of the subject, the method comprising the steps, executed by the arithmetic operation device, of:
    calculating a blood pressure value of the subject from a change in internal pressure of the air bladder placed on the measurement site of the subject;
    obtaining a pulse wave waveform for one beat from the change in internal pressure;
    specifying a time difference between an appearance of an ejected wave and an appearance of a reflected wave in the pulse wave waveform for one beat;
    determining a difference in respective propagation paths of the ejected wave and the reflected wave from a heart to the measurement site based on the blood pressure value and a value representing a distance from an aortic root to an iliac artery bifurcation that is stored in advance; and calculating the pulse wave velocity of the subject based on the propagation path difference and the time difference.

* * * * *